United States Patent [19]

Yabusaki et al.

[11] Patent Number: 4,599,303

[45] Date of Patent: Jul. 8, 1986

[54] NUCLEIC ACID HYBRIDIZATION ASSAY EMPLOYING PROBES CROSSLINKABLE TO TARGET SEQUENCES

[75] Inventors: Kenichi K. Yabusaki, Albany; Stephen T. Isaacs, Orinda; Howard B. Gamper, Jr., San Rafael, all of Calif.

[73] Assignee: HRI Associates, Inc., Emeryville, Calif.

[21] Appl. No.: 560,430

[22] Filed: Dec. 12, 1983

[51] Int. Cl.[4] ...................... C12Q 1/68; G01N 33/566
[52] U.S. Cl. .......................................... 435/6; 935/77; 935/78; 436/501
[58] Field of Search ...................... 435/6; 935/77, 78; 436/501

[56] References Cited

U.S. PATENT DOCUMENTS 3,798,131  3/1974  Rounds et al. ........................ 435/6

FOREIGN PATENT DOCUMENTS 0070687  1/1983  European Pat. Off. .............. 935/78

OTHER PUBLICATIONS

Ashley et al, Analytical Biochem., 140(1984) 95–103.
Dutton et al., Analytical Biochem., 140(1984) 121–128.
Griffith et al, J. Mol. Biol., 157(1982) 321–330.
Wu et al., Proc. Natl. Acad. Sci. USA, 78(1981) 7059–63.
Wollenzien, P. L. and Cantor, C. R., "Marking the Polarity of RNA Molecules for Electron Microscopy by Covalent Attachment of Psoralen-DNA Restriction Fragments", Proc. Natl. Acad. Sci. USA, 79:3940–3944 (1982).

*Primary Examiner*—Christine M. Nucker
*Attorney, Agent, or Firm*—Limbach, Limbach & Sutton

[57] ABSTRACT

Novel methods and reagents for determining the presence of specific nucleic acid base sequences by employing crosslinking reactions of unique molecules capable of forming covalent bonds which are bonded with various labels or ligands for amplication.

Single stranded nucleic acid probes are employed which contain complementary base sequences to nucleic acid target molecules. By first hybridizing and then forming covalent bonds between the probe and target the amount of label in the crosslinked hybrid can be measured as an extremely sensitive method for assaying for specific nucleic acid sequences.

37 Claims, No Drawings

NUCLEIC ACID HYBRIDIZATION ASSAY EMPLOYING PROBES CROSSLINKABLE TO TARGET SEQUENCES

DESCRIPTION

1. Technical Field

This invention relates to probes for the identification of specific nucleic acid base sequences and more particularly to complementary DNA and/or RNA probes for the location of specific DNA and/or RNA sequences on single stranded complementary sequences.

2. Background Art

The application of recombinant DNA techniques is emerging as a powerful tool in the area of molecular diagnostic medicine. For example, the development of DNA and RNA molecular probes for the detection of viral and bacterial genomes and genetic defects in mammalian chromosomes may replace current immunochemical approaches.

Determining the presence of a specific virus, bacterium, and other organisms by noncultural methods and/or genetic defects in mammalian cells by detecting the presence of specific genomic regions has been made possible by the methods of Ross et al. Proc. Nat. Acad. Sci. USA, 69, 264 (1972), Harrison et al., Nature (London) 239, 219 (1972), Sullivan et al., J. Biol. Chem. 248, 7530 (1973), and Southern, J. Mol. Biol., 98, 503 (1975). Here the DNA or RNA from e.g. a particular virus, or DNA from mammalian cells is digested with restriction endonucleases, enzymes which cut DNA at specific nucleotide sequences and produce smaller fragments. The fragments are separated by molecular weight using gel electrophoresis and the gel layered with a filter that absorbs the nucleic acid fragments. The filter is incubated with a radioactively labelled probe (usually phosphorus-32 ($^{32}P$)) consisting of a single strand of DNA or RNA with base sequences complementary to a genomic region near the gene being studied. The probe hybridizes to only those fragments containing a complementary nucleic acid sequence and the hybrids are detected by autoradiography. The presence of characteristic hybrid nucleic acid banding patterns on the autoradiogram is indicative of the presence of a specific viral or bacterial genome or for example, a gene defect in a mammalian chromosome.

The use of $^{32}P$ nuclide as a nucleic acid probe label is not desirable for several reasons. First, $^{32}P$ has a relatively short half life of 14.3 days. Consequently, the complementary probe DNA must be prepared just prior to the hybridization procedure. Secondly, the high decay energy of $^{32}P$ creates more rigid handling problems and undesirable hazards. It would therefore be advantageous in most cases to utilize a label which is less hazardous and prolongs the shelf life of the probe. High specific activity tritium labelled probes present one alternative. While tritium has not generally been found useful in previous hybridization methods which requires extended exposure times for detection by autoradiography, a solution method which detects labelled probe by liquid scintillation counting would be highly sensitive and desirable. Another less energetic isotope than $^{32}P$ but with a long half life is carbon-14.

The development of non-radioactive labeling of nucleic acid probes presents another alternative. One of the most sensitive non-radioactive DNA labelling systems is described by Langer et al., Proc. Nat. Acad. Sci. USA, 78, 6633 (1978). The system is based on the incorporation of a biotinylated deoxyuridine triphosphate into the DNA probe by the nick translation procedure. The resultant biotinylated DNA probe is stable and behaves as does a non-biotinylated DNA probe. Detection of the biotinylated DNA has been applied to the detection of specific DNA and RNA sequences in fixed cells or in tissues following in situ hybridizations and also in hybridizations of DNA fragments separated by gel electrophoresis and transfer onto nitrocellulose filters. The detection of the hybridized biotinylated probe is accomplished by either fluorescent antibody or enzyme amplification techniques. These techniques are further described by Gardner, BioTechniques, 1, 38 (1983) and Lewin, Science, 221, 1167 (1983).

Other non-radioactive methods which have been described involve conjugating a fluorescent molecule such as tetramethylrhodamine or fluorescein isothiocyanate, to the 3'-terminus of single stranded RNA. These fluorescent RNA probes have been applied to cytochemical hybridizations, Bauman et al., J. Histochem. Cytochem., 29, 227 238 (1981).

DISCLOSURE OF THE INVENTION

The present invention provides methods and reagents for determining the presence of specific DNA and RNA base sequences on single stranded target polynucleotides. Application of the methods and reagents will allow for the detection of specific bacterial and viral genomes as well as certain defects in mammalian chromosomes. The method involves the preparation of a specific single stranded ribonucleic acid or deoxyribonucleic acid molecule into which a bifunctional crosslinking molecule has been covalently incorporated. The incorporation is such that the crosslinking molecule retains the capacity to undergo a second addition to the nucleic acid of the bacterial, viral, or mammalian chromosome which is the target for the probe.

The single stranded DNA or RNA probe is designed so that its nucleic acid base sequence is complementary to a unique region of the bacterial, viral, or mammalian chromosome target sequence. The nucleic acid, for example, from a blood, tissue, or cell sample is reacted with the probe under conditions where hybridization of the probe with the target will occur. Following hybridization, the sample is subjected to a photochemical or chemical procedure which causes cross linking of the probe to the target complementary sequence. If no target genomic sequence is present, then no crosslinking of the probe will occur. In some cases hybridization of the probe to the target will preceed both reactions of the bifunctional crosslinking reagent.

Following crosslinking the uncrosslinked probe is separated from covalently crosslinked probe-target complex using one of several procedures which differentiate between single stranded probe and double stranded probe-target complex. The procedures include, for example, gel filtration, hydroxylopatite chromatography, enzymatic digestion, alkaline hydroysis, and photoreversal or chemical reversal of uncrosslinked crosslinking molecules.

The presence of crosslinked hybrid is diagnostic for the presence of the particular viral, bacterial, or mammalian chromosome target. Normally detection of the target hybrid is accomplished by incorporation of a radioactive or nonradioactive label on the crosslinking molecule bound to the probe. Ocassionally the label is incorporated in the probe as in the target. Having the label bound only to the crosslinking molecule monoadducted to the probe provides an extremely sensitive method for determining the presence of extremely low concentrations of specific nucleic acid base sequences. In the absence of the target genome, all the label remains bound to single stranded probe. In the presence of the target genome the reagent containing the label becomes crosslinked resulting in a double stranded nondenaturable hybrid structure. Clear separation of the two classes of nucleic acid allows for the unambiguous determination of the presence or absence of the target genome based on the presence or absence of label in double stranded form.

Normally, the hybridization and crosslinking steps are done in solution without the need for electrophoretic gel separations or blotting procedures. The simplicity of the required manipulations, high sensitivity, and low background of the procedure have clear advantage to other hybridization assays. Application of the crosslinking procedure to in situ hybridization and other procedures which involve the stabilization of hybrids should simplify the protocols and increase their sensitivity.

BEST MODE FOR PRACTICING THE INVENTION

This invention provides methods and reagents for determining the presence of extremely low concentrations of specific nucleic acid base sequences by hybridizing and crosslinking by, for example, photochemical or chemical techniques a target DNA or RNA containing a known base sequence with a polynucleotide probe containing labelled crosslinking compounds as monoadducts, in which the probe has a complementary base sequence to the target DNA or RNA.

The nucleic acid probe will consist of chemically synthesized or biologically prepared DNA or RNA polynucleotides from 10–200 bases in length or longer single-stranded sequences including messenger RNAs and single-stranded DNA or RNA genomes. The labelled crosslinking molecules will be directly incorporated into synthetic polynucleotides at the time of synthesis through the use of appropriately modified nucleoside or nucleotide derivatives. Alternatively, the labelled crosslinking molecules will be introduced onto the probe through photochemical or chemical monoaddition. Although the crosslinking molecule will normally contain the label which permits subsequent detection, that label can alternatively reside directly on the nucleic acid probe or target.

Hybridization will usually involve denaturation of the target DNA or RNA in the presence of a large molar excess of monoadducted probe. After renaturation, the hybridized probe will be photochemically or chemically crosslinked to the target DNA or RNA. The crosslinkage permits free probe to be removed from the target DNA or RNA under denaturing conditions which would normally lead to the loss of the hybridized probe as well. This methodology will result in very low backgrounds and correspondingly high sensitivities.

Several protocols will be used to remove free probe from hybridized and crosslinked probe. The first will consist of gel filtration of the hybridization reaction mixture through an appropriate molecular weight sizing column under denaturing conditions. The second will involve enzymatic digestion of all the single-stranded nucleic acid in the hybridization reaction mixture (which will include free probe as well as much of the target nucleic acid) and subsequent recovery of the hybridized probe (which will be double-stranded). Digestion can be accomplished by using for example, nuclease S1, mung bean nuclease, nuclease Bal 31, exonuclease VII, or T4 DNA polymerase. Double-stranded nucleic acid can be recovered by, for example, chromatography through hydroxyl apatite or benzyoylated naphthoylated diethylaminoethyl cellulose (BND cellulose) or by acid precipitation and collection on a glass fiber filter.

A third technique which can be used separately or in combination with one of the above protocols involves photoreversal or chemical reversal of the monoadducted crosslinking molecules on free probe and their removal by, for example, gel filtration, ethanol precipitation, or acid precipitation. The crosslinked probe molecules associated with the target DNA or RNA will not photoreverse or chemically reverse under the conditions employed. This technique reduces the background since the label is normally contained on the crosslinking molecule.

A fourth isolation technique, which will only be applicable to RNA probes in the presence of a target DNA can involve, for example, enzymatic digestion or alkaline hydrolysis of the total RNA to free nucleoside monophosphates followed by recovery of the target DNA by, for example, gel filtration, ethanol precipitation, or acid filtration. In this protocol all of the labelled crosslinking molecules will be lost except for those covalently linked to the target DNA.

A fifth isolation technique can utilize a chemical linkage between the probe and a solid support such as silica or controlled pore glass, for example.

Detection of the hybridized probe will normally be accomplished by measuring the label on the crosslinking molecule after hybridization, photochemical or chemical crosslinking, and removal of free probe. The particular label on the crosslinking molecule will include, e.g. a radioactive nuclide introduced by replacing a proton with tritium, carbon-14 or other radioactive atom or a ligand analog modified with a linker group to provide a linking site to the crosslinking molecule. The ligand, and linker group if present, will have chemical characteristics or functionalities such that a small radioactive nuclide labeled molecule or chromogenic, fluorogenic, luminescent molecule, or magnetic particle can be attached to the ligand or linker group. The ligand will have chemical characteristics such that a receptor molecule is available or capable of being ellicited, such as an antibody molecule to the ligand. The receptor molecule can be conjugated to a radioactive nuclide, chromogenic, fluorogenic, luminescent dye molecule, magnetic particle or an enzyme system capable of generating a chromogenic, fluorogenic, and/or luminescent product via appropriate substrates.

Various methods or protocols may be employed in measuring the amount of the labels. These protocols can include for example, radioimmunoassay (RIA), immunoradiometric assay (IRMA), sandwich IRMA, fluoroimmunoassay (FIA), chemilumenescent assays, bioluminescent assays, and enzyme linked immunosorbent assays (ELISA) among others.

The particular target DNA or RNA whose specific base sequence is known is referred to as a target. The particular polynucleotide containing the labeled crosslinking molecules as monoadduct and containing a base sequence complementary to the target is referred to as a probe. The joining together of both target and complementary probe polynucleotide by the mechanism of base pairing through hydrogen bonds between purine and pyrimidine bases is referred to as hybridization and the resultant complex termed a hybrid.

THE CROSSLINKING REAGENT

The crosslinking reagent for use in the hybridization assay can be any bifunctional molecule which covalently crosslinks the probe molecule to the target genome. Generally the crosslinking reagent will be a bifunctional photoreagent which will be monoadducted to the probe molecule leaving a second photochemically reactive residue which can bind covalently to the target genome upon photoexcitation. Occasionally the crosslinking molecule will be a mixed chemical and photochemical bifunctional reagent which will be non-photochemically bound to the probe molecule or a modified probe molecule via a chemical reaction such as alkylation, condensation or addition, followed by photochemical binding to the target genome or modified target genome. Bifunctional chemical crosslinking molecules, activated either catalytically or by high temperature following hybridization, would also occasionally be employed.

Examples of bifunctional photoreagents include furocoumarins, benzodipyrones, and bis azides such as bis-azido ethidium bromide. Examples of mixed bifunctional reagents with both chemical and photochemical binding moieties include haloalkyl-furocoumarins, haloalkyl benzodipyrones, haloalkyl-courmarins and various azido nucleoside triphosphates.

The crosslinking reagent will normally possess one of the following active moieties:

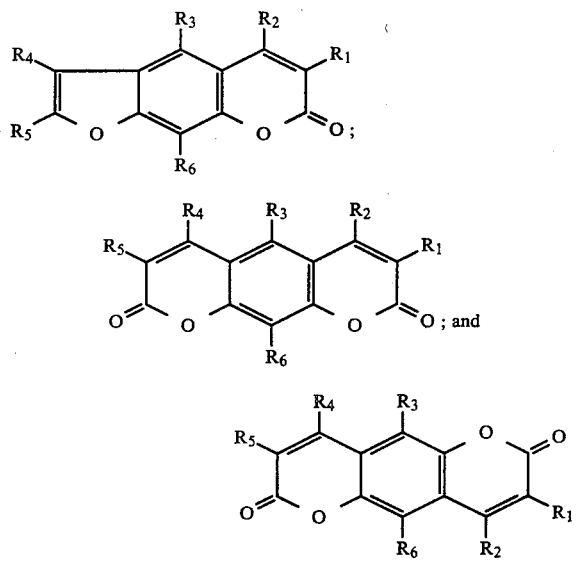

wherein R1-R6 are a member selected from the group consisting of, for example, H, CH₃, CH₂Cl, CH₂Br, CH₂I, CH₂OH, CH₂OCH₃, CH₂NH2, N₃COOH, COOCH₃, COOCH₂CH₃, NH₂, NO₂, CF₃, CCl₃, CH(CH₃)₂, C(CH₃)₃, Cl, Br, I, F.

The linear furocoumarins (psoralens) exemplify bifunctional chemical or photoreagents for use in the hybridization assay. The structure (1) of psoralen (i.e., where R1=R2=R3=R4=R5=R6=H) is shown above. Some naturally occurring and potentially useful psoralens include 8-methoxypsoralen (i.e., R1—R5=H; R6=OCH₃), 5-methoxypsoralen (i.e., R1=R2=R4=R5=R6=H; R3=OCH₃), and 4, 5', 8-trimethylpsoralen (i.e., R1=R3=R4=H; R2=R5=R6=CH₃). In addition to these compounds, there are 30-40 other naturally occurring psoralens which have been reported many of which are useful in practicing the present invention.

Any psoralen which can efficiently crosslink DNA could be used in the hybridization assay. Synthesis of a wide variety of psoralens is now straight forward and new compounds can readily be prepared. Changing the type and position of substituents on the psoralen has a dramatic effect on the various steps in the reaction with nucleic acid [Isaacs et al., in *Trends in Photobiology*, Helene et al., eds., p. 279 (1982)]. Parameters such as solubility, photochemical or thermal stability, dark binding affinity to DNA, rate of photochemical or thermal binding to DNA, quantum yield of photochemical addition, type of adduct formed (for example furan-side or pyrone-side in the case of psoralens), and extent of crosslink formation are all amenable to control by a combination of synthetic design, buffer conditions during energy activation and in the case of irradiation, the intensity and wavelength of light used.

While psoralen contains the key elements necessary for the hybridization assay, other reagents are possible. For example, both cis-benzodipyrone (2) and trans-benzodipyrone (3) are potential nucleic acid crosslinking agents. Both compounds are reactive towards pyrimidine bases in solution and photo-induce mutation in certain *Bacillus subtilis* strains [Harter et al., Photochemistry and Photobiology 20, 407-413 (1974)]. Another approach uses a probe which incorporates an azide substituted base in the polynucleotide probe which would be competent to crosslink probe and target via a light activated nitrene intermediate. Such azidoadenosine compounds have been prepared. Other azide type modified bases, incorporated into polynucleotides, are within the capability of an ordinary skilled chemist.

THE RADIOLABELLED CROSSLINKING REAGENT

Generally the radiolabelled crosslinking reagent will be prepared by chemical synthesis which incorporates tritium, carbon-14, or other radioactive atoms into the structure. High specific activity radio-labelled crosslinking reagents are considered desirable for the hybridization assay and would determine the ultimate sensitivity of the method. The synthetic schemes developed for the preparation of for example radiolabelled psoralens illustrate the general approach which can be used for the preparation of a wide variety of radiolabelled crosslinking reagents. The particular method used would depend on the characteristics of the particular crosslinking reagent to be labelled.

The synthetic schemes developed for the preparation of labeled reagents such as psoralens are of two basic types: (1) exchange reactions with tritium gas or HTO, providing randomly labeled psoralens with relatively low specific activities; and (2) site-specific incorporation of either carbon-14 or tritium by alkylation with labeled alkyl halides, reduction with sodium borotritide, catalytic reduction with tritium gas, or hydrogenolysis with tritium gas. Site-specifically labeled psoralens typically have specific activities which are much higher than psoralens prepared by exchange procedures.

To provide high specific activity psoralens which incorporate the isotope at known positions in the molecule, four methods have been used [Isaacs et al., J. Labeled Compounds & Radiopharmaceuticals 19, 345 (1982); Isaacs et al., J. of the National Cancer Institute, (1983) in press].

(A) Alkylation with Carbon-14 or Tritium Labeled Alkyl Halides

Both 8-[(3H$_3$)-methoxy] psoralen and 5-[(3H$_3$)-methoxy] psoralen have been synthesized by demethylation to the corresponding phenol followed by alkylation with tritium labeled methyl iodide. The specific activities of these compounds were 2–3 Ci/mmol. The analogous carbon-14 labeled 8-MOP and 5-MOP have also been prepared using carbon-14 labeled methyl iodide.

This procedure is applicable to psoralen derivatives with substituents appropriate for dealkylation followed by re-alkylation with the labeled alkyl halide.

(B) Sodium Borotritide Reduction

Psoralens which contain formyl or alkyl ketone substituents can be reduced with sodium borotritide to provide the corresponding labeled primary and secondary alcohols with incorporation of tritium at the carbonyl carbon. This procedure has been used to synthesize 4'-[3H$_1$)-hydroxymethyl]-4,5', 8-trimethyl-psoralen (HMT) from 4'-formyl-4,5', 8-trimethylpsoralen and 4'-dl-[(3H$_1$)-hydroxy-ethyl] 4,5', 8-trimethylpsoralen from 4'-acetyl -4,5', 8-trimethylpsoralen. HMT with a specific activity of 12 Ci/mmol has been prepared from commercially available sodium borotritide (48 Ci/mmol). Labelled HMT can be readily converted to 4'-[(3H$_1$)-chloromethyl]-4,5',8-trimethylpsoralen with thionyl chloride, which can then be converted to a number of labeled psoralens. The highly water soluble 4'-[(3H$_1$)-aminomethyl]-4,5', 8-trimethylpsoralen at 12 Ci/mmol has been prepared by this method.

(C) Catalytic Reduction with Tritium Gas

Catalytic reduction with tritium gas has been used to prepare a variety of labeled psoralens for which alkylation or sodium borohydride reduction cannot be applied. The specific activity of psoralens prepared by catalytic reduction has been in the 3–20 Ci/mmol range. This procedure produces tritiated psoralens with incorporation at the 3,4, 4', and 5' carbons. Selective labeling at the 4' and 5' carbons has been accomplished using this procedure since the 4', 5' (furan) double bond is reduced prior to and faster than the 3, 4 (pyrone) double bond. Partial reduction gives a (4', 5'-$^3$H$_2$) psoralen which can be isolated and dehydrogenated to provide furan-side labeled compounds. Alternatively, full reduction to (3,4,4', 5'-3H4)) psoralen provides compounds labeled at both the furan and pyrone double bonds.

The extent of incorporation of tritium depends upon the particular solvent and catalyst combination used in the reduction. Glacial acetic acid with 10% palladium on charcoal provides for rapid reduction along with acceptable isotope incorporation. Dehydrogenation is typically accomplished by refluxing the reduced psoralen is diphenylether in the presence of palladium on charcoal. Using catalytic reduction (3,4,4', 5'-$^3$H$_4$) psoralen (4.4 Ci/mmol), (3,4'-$^3$H$_2$)-4, 5', 8-trimethylpsoralen (17.6 Ci/mmol), (4,5'-$^3$H$_2$)-5-methylisopsoralen (7.4 Ci/mmol), and (4',5'-$^3$H$_2$)-3-carbethoxypsoralen (20 Ci/mmol) have been prepared [Isaacs—et al., J. of the National Cancer Institute, (1983) in press]. This procedure is applicable to unsubstituted psoralens, alkyl psoralens, and psoralens with other substituents stable to catalytic reduction.

(D) Hydrogenolysis with Tritium Gas

The synthesis of (3-$^3$H$_1$)-4'-aminomethyl-4,5', 8-trimethylpsoralen (AMT) by hydrogenolysis of 3-bromo-4'-phthalimindomethyl-4,5', 8-trimethylpsoralen has been reported. Hydrazinolysis of this compound yielded labeled AMT with a specific activity of 7.46 Ci/mmol [Liebman, A. A. and Delaney, C. M., J. of Labeled Compounds & Radiopharmaceuticals 18(8), 1167 (1981)].

In summary, several methods for preparing high specific activity tritium labeled psoralens are available. Using either borotritide or catalytic reduction, specific activities in the 10–20 Ci/mmol range have been achieved. By modification of these known procedures, such as using a non-protic solvent for catalytic reduction with carrier free tritium gas, even high specific activities are possible (40–60 Ci/mmol).

Nonradioactive Labels

Nonradioactive labels, herein called "label(s)", can be divided into two categories (i) chromogenic, fluorogenic, and/or chemiluminescent dyes or (ii) ligands. The label is attached to the crosslinking molecule as shown by the following scheme:

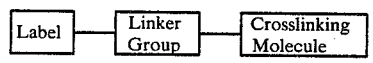

Where a linking group is used it will normally consist broadly of from 1 to 40 atoms, more usually from six to 20 atoms and more preferably from 8 to 15 atoms in the backbone of the chain bonding the label to the crosslinking molecule. Where cyclic structures are involved, the cylic structure will be equated to the number of atoms so as to provide a similar length to the chain.

The linking group can be from about 1 to 40 atoms composed of, for example, carbon, hydrogen, oxygen, nitrogen, phosphorus, and sulfur and more preferably 4 to 30 atoms.

The following tabulation shows illustrative examples of various linking groups varying with the functionalities present on the label and the crosslinking molecule. Except as indicated, the linking group satisfies one to two valences on the label and crosslinking molecule functional groups to which it is bonded.

| Label | Crosslinking molecule |
|---|---|
| amino (—NH—) or hydroxyl (OH) or carboxyl (CO—) | primary amino (—NH$_2$), hydroxyl (OH), secondary amino (—NRH), mercapto (—SH) |

Linker Groups

N—(CH$_2$)$_2$—O—(CH$_2$)$_2$—O—(CH$_2$)$_2$—

$$\overset{O}{\underset{\|}{-C-}}$$

$$\overset{S}{\underset{\|}{-C-}}$$

$$-\overset{O}{\underset{\|}{C}}-(CH_2)_n-\overset{O}{\underset{\|}{C}}-$$

-continued

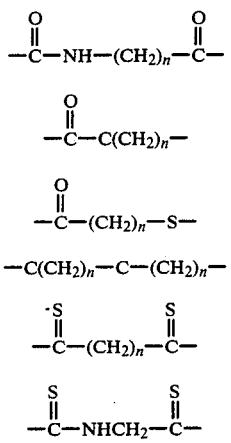

wherein n = 1 to 12

Dyes

The dyes are normally of from eight to 40 carbon atoms more usually of from nine to 30 carbon atoms. The dyes further normally contain from one to 10 heteroatoms usually oxygen, nitrogen or sulfur and normally contain zero to 10 halogen atoms usually iodine, bromine, chlorine, or fluorine. Examples of chromogoenic dyes include phenol sulfonepthalein and analogs of tetrazolium.

Examples of fluorogenic dyes are fluorescein isothiocyanate, dichlorotriazinylamino fluorescein, morpholinorhodamine isothiocyanate, tetramethylrhodamine isothyiocyanate and 4-acetamido-4-isothiocyanostilbene-2 with 2'-disulfonic acid.

Examples of chemiluminescent dyes are 5-amino-2,3-dihydropthalazine-1,4-dione (luminol), derivatives of isoluminol and acridinium esters.

Ligand

Any ligand may be employed for which an appropriate receptor may be found having satisfactory specificity for the ligand.

Broadly, ligands are chosen from organic compounds of from 100–10,000 daltons molecular weight, usually of from 125 to 3,000 daltons molecular weight, more usually 125 to 1,000 daltons molecular weight. The ligand will usually have from about eight to 100 carbon atoms and from about one to 50 heteroatoms.

The ligands are generally compounds of carbon, nitrogen, oxygen, sulfur, phosphorus, halogens and metals, primarily as their cations such as e.g., the alkaline earth metals and rare earth metals.

Structurally, the ligands are monomers or polymers, acyclic, mono or polycyclic having carbocyclic or heterocyclic rings. The ligands will have various functionalities such as halo, oxocarbonyl, nonoxocarbonyl, amino, oxy, hydroxy, aryloxy, alkyloxy, cycloallyloxy, thiooxy, dithio and hydrazo.

The ligands can also have various relationships to the receptor. First are antigens which when introduced into the bloodstream of a vertebrate results in the formation of antibodies to the antigen. Second are haptens which must be bound to an immunogenic carrier such that the hapten-carrier when introduced into the bloodstream of a vertebrate results in antibody formation against the hapten. The third category of ligands includes those which have naturally occurring receptors such as biotin of which avidin, a protein, is the receptor.

Examples of psoralen analogs which have biotin attached through a linker group are as follows:

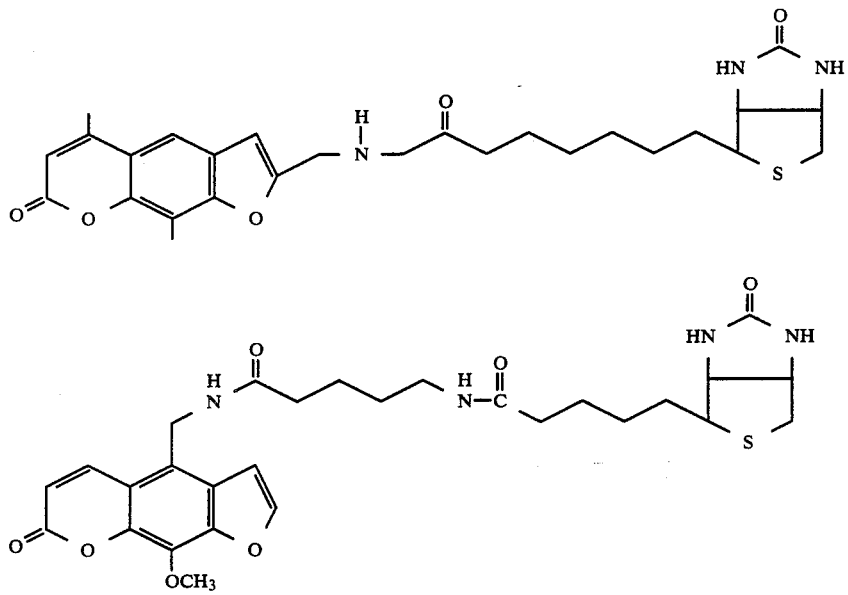

Other ligands include specific monosaccharides of which specific lectins are the receptors. Alternatively, the immunogenic response can be developed in vitro.

Receptor

For the most part, in this invention, the receptor will be a macromolecule which has sites that recognize specific structures. The macromolecules of greatest interest are proteins. These include antibodies and natural receptors such as avidin and lectins for example. The receptors can be conjugated with chromogenic, fluorogenic, and/or chemiluminescent dyes or an enzyme system capable of generating a chromogenic, fluorogenic, and/or luminescent product via appropriate substrate(s).

In the case where biotin is the ligand and avidin the receptor, biotinylated enzymes such as, for example, biotinylated-alkaline phosphomonoesterase, beta-galactosidase, glucose oxidase, horse radish peroxidase, and pyruvate kinase can be complexed to the three remaining biotin binding sites on avidin which is bound to the biotin ligand label on the probe. After subsequent removal of the excess biotinylated enzyme of choice, an appropriate substrate for the specific enzyme used is added which generates a chromogenic, fluorogenic, and/or luminescent product which can be detected by conventional methods and/or instruments. Another example where biotin is the ligand and avidin the receptor involves the use of a biotinylated protein such as bovine serum albumin to which fluorescent dye molecules such as fluorescein isothiocyanate has been conjugated. Here the fluorescent biotinylated bovine serum albumin can complex to the three remaining biotin binding sites on avidin bound to the probe to generate a fluorescent tag.

Limits of Detection

With radio labelled crosslinking molecules, the sensitivity of the assay is determined by the specific activity of the crosslinking reagent used. The sensitivity of the assay can be increased by (a) increasing the specific activity of the crosslinking molecule; (b) increasing the number of crosslinking molecules per probe molecule, (c) increasing the number of probe molecules which are hybridized to the target DNA or RNA, and (d) the use of higher decay energy radionuclides.

EXPERIMENTAL

The following examples are provided by way of illustration and are not to be construed as limiting the invention.

EXAMPLE 1

High Specific Activity Tritium Labelled cis-Benzodipyrone and trans-Benzodipyrone Cis or trans-benzodipyrone (1 mmol), palladium on charcoal (10%, 1 mmol) and an appropriate solvent (e.g. glacial acetic acid) are placed in a small round bottom flask, the mixture frozen and atmospheric gases removed. The system is charged with carrier free tritium gas and the mixture stirred at 20°–80° C. until no more tritium gas is absorbed. The residual tritium is removed, the catalyst filtered off and the solvent evaporated. The residue is applied to a silica gel chromatography column and the [3,4,6,7-$^3$H$_4$]-3,4,6,7-tetrahydrobenzodipyrone isolated by elution with chloroform/methanol. The tetrahydro compound is then refluxed in diphenylether with an equimolar amount of 10% palladium on charcoal until all the starting material is consumed. 3,4,6,7,-$^3$H$_4$-benzodipyrone is isolated by preparative column chromatography then purified by high pressure liquid chromatography (2–40 Ci/mmol).

EXAMPLE 2

Synthesis of Polynucleotide with Thymidine: 8-Methoxypsoralen Phosphoramidite

DNA or RNA polynucleotides can be chemically or enzymatically synthesized by established procedures. [T. C. Atkinson, BioTechniques March-April, 6-10 (1983)] When a particular nucleoside monophosphate is modified to contain a labelled crosslinking molecule the latter can be directly incorporated into the polynucleotide at the time of synthesis.

For example, thymidine monoadducted to psoralen, 8-methoxypsoralen, 4,5',8-trimethylpsoralen and 4'-hydroxymethyl-4,5',8-trimethylpsoralen has been prepared by reaction of the psoralen derivative with deoxyribonucleic acid followed by enzymatic or chemical hydrolysis of the DNA and chromatographic isolation of the thymidine:psoralen monoadduct [Straub, et al. J. American Chemical Society 103, 2347–2355 (1981); Kanne et al., Biochemistry 21, 861–871, (1982)]. Alternatively, the thymidine:8-methoxypsoralen monoadducts have been prepared from the monomers by irradiating a thin film of the two compounds mixed together [Shim et al., Photochem. Photobio. 38, 265–271 (1983)]. The uridine:4'-hydroxymethyl-4,5',8-trimethylpsoralen monoadducts have been prepared by reacting 4'-hydroxymethyl-4,5', 8-trimethylpsoralen with ribonucleic acid followed by the enzymatic or chemical hydrolysis of the RNA and chromatographic isolation of the uridine:4'-hydroxymethyl-4,5', 8-trimethylpsoralen monoadducts [Isaacs et al., Photochem. Photbio. 37 (supplement), s100 (1983)]. All of the above pyrimidine:psoralen monoadducts can be suitably modified for use in polynucleotide synthesis.

For example, the furan-side monoadduct between thymidine and 8-methoxypsoralen, prepared as described above, is reacted with 4,4'-dimethoxytrityl chloride at room temperature in an appropriate anhydrous solvent to give the 5'-dimethoxytrityl thymidine:8-methoxypsoralen monoadduct. Following purification by high pressure liquid chromatography this compound is reacted with chloro-N,N diisopropylamino methoxyphosphine at room temperature in an appropriate solvent to give the 5'-dimethoxytritylthymidine phosphoramidite: 8-methoxypsoralen monoadduct. This compound is then used as an activated protected nucleoside phosphoramidite in a typical phosphite triester polynucleotide synthesis. The stereochemistry of the 8-methoxypsoralen moiety is correct (i.e. cis-syn) for subsequent crosslink formation when hybridized to the complementary sequence.

EXAMPLE 3

Isolation of RNA and DNA Probes From Biological Sources with Subsequent Monoaddition of the Crosslinking Reagent Alternatively, probe DNA or RNA can be isolated from biological sources and subsequently reacted with the labelled crosslinking reagent of interest. Single-stranded DNA can be obtained directly from single-stranded viral genomes such as M13 or φX174 or indirectly from double-stranded genomes or plasmids by strand separation. The size of the probe will be controlled by enzymatic processing including exonuclease treatment of single stranded DNA and restriction or Bal 31 digestion of double stranded DNA. The DNA probe can also be prepared enzymatically from appropriate nucleic acid subtrates. For example, DNA could be obtained from mRNA using reverse transcriptase. RNA probes can be directly obtained from biological sources in the form of viral genomes (R17, F2, QB) or mRNA. Alternatively, the RNA can be enzymatically synthesized in vitro from appropriate templates. For example, transcription off a double stranded DNA template with RNA polymerase would generate probe RNA.

These biologically prepared DNA or RNA probes are then monoadducted to the the crosslinking reagent by either photochemical or chemical addition of the crosslinking molecule. For example, single stranded φX174 which contains one 4'-hydroxymethyl-4,5',8-trimethylpsoralen for every 50 bases is prepared as follows. Single stranded φX174 DNA is obtained as described by Piette et al., Photochem. Photobio. 35, 705–708 (1982).

A 50 μl solution containing 0.1 μg φX174SS DNA/ml in 10 mM Tris (pH 8.0), 1 mM EDTA and 5 or 60 mM NaCl was mixed with $^3$H-HMT at the ratio of one drug per ten base pairs. The DNA psoralen mixture was irradiated at 10° C. with two 400 W. General Electric mercury vapor lamps. The irradiation chamber contained a Cobaltous nitrate solution (40% W/W) acting as a filter which removes light outside the range of 340 to 380 nm. Photoreacted DNA was taken from the irradiation chamber and noncovalently bound drugs were removed from the DNA by two chloroform and two ether extractions followed by two ethanol precipitations.

An alternate approach for preparing monoadducted DNA and RNA probes is the following. An polynucleotide of 20–800 bases is hybridized to its complementary sequence which has been inserted into M13 or single stranded PBR322 by well established genetic engineering methodology. The hybrid molecule (0.1 OD), 8-methoxypsoralen (35 μg/ml) in a buffer consisting of tris hydrochloride (0.01 M), and EDTA (0.001 M) at pH 7.5 is irradiated at 320–380 nm for three hours. Following irradiation, the reaction mixture is extracted with chloroform three times then ethanol precipitated. The pellet is resuspended in 0.1 ml distilled water then irradiated 10–20 minutes at 254 nm. Naturally, the specific wavelengths of light recited are optimized for the specific hybrids employed in this example. Other hybrids would of course be irradiated by the light of differing wavelengths for optimum results.

The reaction mixture is loaded on an agarose or polyacrylamide gel under denaturing conditions and electrophoresed. The band containing the monoadducted polynucleotide is excised, electroeluted, purified by ion exchange chromatography and ethanol precipitated. In some cases, the purified monoadducted polynucleotide is randomly digested to small fragments in the 20–50 base range either chemically or enzymatically.

EXAMPLE 4

Preparation of Non-Radiolabeled Crosslinking Reagent

As an example of a fluorescent dye labelled crosslinking reagent, the preparation of 4'-N-(N-hexylamido-N-fluoresceinylurea) -4,5',8-trimethylpsoralen will be described.

4'-aminomethyl-4,5',8-trimethylpsoralen is reacted with the N-hydroxysuccinimide ester of 6-N-tert-butoxycarbonyl-caproic acid in anhydrous dimethylformamide: methylene chloride 1:1 v/v. The resultant 4'-N-(N-hexylamido-N-tert-butoxycarbonyl)-4,5', 8-trimethylpsoralen is treated with mild acid to remove the tert-butoxycarbonyl group and purified on a silicic acid column using chloroform and methanol mixtures. The resultant 4'-N-(N-hexylamido-6-amino)-4,5',8-trimethylpsoralen is reacted with an excess of fluorescein isothiocyanate in anhydrous dimethylformamide or dimethylsulfoxide and the resultant 4'-N-(N-hexylamido-N-fluoresceinylurea)-4,5',8-trimethylpsoralen purified by preparative thin layer chromatography in the dark.

As an example of a ligand labelled crosslinking reagent, the preparation of 4'-N-(N-hexylamido-N-biotinamido)-4,5', 8-trimethylpsoralen will be described.

The N-hydroxysuccinimide ester of biotin is reacted with 6-aminocaproic acid in anhydrous dimethylformamide. The resultant caproamidobiotin is converted to its N-hydroxysuccinimide ester by reaction with N,N'-carbonyldimidazole and N-hydroxysuccinimide in anhydrous dimethylformamide. To the resultant mixture containing the N-hydroxysuccinimide ester of caproamidobiotin is added an excess of 4'-aminomethyl-4,5', 8-trimethylpsoralen which has been previously dissolved in anhydrous methylene chloride. The progress of the reaction is monitored by thin layer chromatography on silica gel G. The resultant 4'-N-(N-hexylamido-N-biotinamido)-4,5', 8-trimethylpsoralen is purified by silicic acid column chromatography using chloroform and methanol mixtures.

EXAMPLE 5

Hybridization of photoaffinity labeled probe DNA to template DNA

The following buffers are used in the hybridization procedure as described by Durnam and Palmiter, Analytical Biochemistry (1983), 131, 385. Buffer A is 10 mM Tris (hydroxymethyl) aminomethane (Tris) and 0.25 mM ethylenediaminetetraacetin acid (EDTA), pH 7.4. Buffer B is prepared as a 10 X stock containing 10% sodium dodecyl sulfate (SDS), 100 mM Tris, 50 mM EDTA, pH 7.5. Hybridization salts (10 X Stock) contains 3 M sodium chloride (NaCl), 100 mM Tris, 20 mM EDTA pH 7.5.

Total nucleic acid (TNA) samples are prepared by homogenizing 25 to 50 mg of a specific tissue or $10^6$ to $10^7$ cells per ml containing the target genome of interest in 1 X Buffer B containing 50–200 micrograms/ml of Proteinase K. The samples are incubated at 45° C. for 1 hour, extracted with phenol/chloroform, re-extracted with chloroform twice, and precipitated with 2 volumes of ethanol. Ethanol-precipitated pellets are resuspended in 0.2 X Buffer B and stored at −20° C. TNA concentrations are determined spectrophotometrically assuming a 1 mg/ml solution has an absorbance at 260 nm of 20. The DNA concentration is determined by either colorimetric or fluorescence assay methods.

Hybridization reactions contain 0.6 M NaCl, 4 mM EDTA, 10 mM Tris, pH 7.5, 40% formamide, 0–20 micrograms of TNA, and 50–100 fold Molar excess of $^3$H psoralen monoadduct probe DNA containing the complementary base sequence to the target genome of interest hereinafter called "pDNA" in a final volume of 0.03 ml. The reactions are carried out in 1.5 ml microcentrifuge tubes. To make the above composition 0.01 ml of the TNA sample is placed in a tube or set of tubes and 0.02 ml of a mixture containing 60% formamide, 0.9% NaCl, 6 mM EDTA, 60 mM Tris, pH 7.4, and 250 to 500 cpm per microliter of pDNA. The latter solution is prepared by combining 6 volumes of deionized formamide, 3 volumes of 10 X hybridization salts, and 1 volume of pDNA in 0.2 X Buffer B to allow sufficient cpm per tube. They are then covered with paraffin oil (approximately 0.1 ml), centrifuged briefly, and incubated at 68° C. for approximately 16-18 hours in the dark. It should be noted that the incubation time can vary from a few hours to several days with a corresponding change in sensitivity.

The hybridized sample(s) are then subjected to irradiation at 340-380 nm at 4° C. in a cooled reaction chamber containing 40% (wt/wt) colbatous nitrate as a liquid filter. The chamber is positioned equidistant between two 400 watt mercury vapor lamps to give a light intensity at the sample of approximately 100 mW/cm$^2$. The irradiation time is 30 minutes which results in the photochemical cross-linking of the hybridized material. Following the hybridization, sample(s) are heat denatured at 100° C. to insure that all unhybridized material and non-crosslinked material is in the single stranded state. After 20 minutes, the sample(s) are cooled to 60° C. and 1 ml of 0.3 M NaCl, 30 mM sodium acetate, 3 mM zinc acetate, and 100 micrograms of herring sperm DNA containing 10 units of S1 nuclease from *Asperqillus oryzae* are added and the sample(s) vortexed thoroughly to ensure that the paraffin oil rises. It should be noted that this solution is prepared by combining 1 volume of 10 X S1 nuclease buffer, 1 volume of herring sperm DNA at 1 mg/ml, 8 volumes of distilled water and 10 units of S1 nuclease per ml of solution. The S1 nuclease reactions are incubated at 55°-60° C. for 1 hour and terminated by the addition of 0.1 ml of 6 M trichloroacetic acid. After vortexing, the samples are filtered onto 2.4 cm Whatman GF/C filters. Filters are first wetted with 3% trichloroacetic acid, 1% sodium pyrophosphate, the sample applied, and then the tube and filter are washed with 3% trichloroacetic acid/1% sodium pyrophosphate three times and finally with 95% ethanol. The filters are then added to 2 ml of toluene-Omnifluor scintillation fluid and counted for 10 minutes each.

In the case of a non-radioisotopic labelled probe (e.g., a biotinylated probe), the filters are placed in a solution containing avidin at 100 micrograms per milliliter in 0.01 Molar Tris-HCl buffer, pH 7.5 for 15 to 60 minutes. The filters are briefly rinsed in the same buffer then placed in a solution containing biotinylated horse radish peroxidase at 100 micrograms per milliliter in 0.01 Molar Tris-HCl buffer, pH 7.5 for 30-120 minutes then washed extensively to remove excess biotinylated horse radish peroxidase. The filters are then placed in a vessel containing a solution of ortho-phenylenediamine at 0.4 mg/ml in 0.025 Molar sodium citrate, 0.05 Molar sodium phosphate, pH 5.0 and containing 0.01% hydrogen peroxide. After a specific time period, the reactions are terminated by the addition of 2.5 Normal sulfuric acid. An aliquot of the colored solution is removed and the absorbance at 492 nm measured versus a blank in which all of the above procedures with the samples were identically performed except no hybridizable target nucleic acid was present. Using this procedure, approximately 20 femtomoles of biotin can be detected as described by Gardner, BioTechniques, 1, 38 (1983). Sensitivity can be increased several fold in the same manner described for the radioactive labelled probe.

We claim:

1. A probe for determining the presence of specific nucleic acid base sequences in nucleic acid target molecules comprising:
   single-stranded nucleic acid molecules having essentially complementary base sequences to defined regions in the nucleic acid target molecules; and
   labeled crosslinking molecules attached to said single-stranded nucleic acid molecules which are capable of forming covalent crosslinks between said single stranded nucleic acid molecules and said target molecules, whereby the presence of said specific nucleic acid base sequence is determined by measuring the amount of labeled probe covalently bound.

2. The probe of claim 1 wherein said label is radioactive.

3. A probe as recited in claim 1 wherein the crosslinking molecule is labeled with a member selected from the group consisting of radioactive nuclides, chromogenic labels, fluorogenic labels, chemiluminescent dyes and ligands.

4. The probe of claim 1 wherein said covalent crosslinks are formed chemically.

5. The probe of claim 1 wherein said covalent crosslinks are formed photochemically.

6. The probe of claim 1 wherein, said crosslinking molecule comprises a member selected from the group consisting of furocoumarins, benzodipyrones and bis azides.

7. The probe of claim 6 wherein said crosslinking molecule comprises bis azido ethidium bromide.

8. The probe of claim 1 wherein said crosslinking molecule comprises a psoralen.

9. The probe of claim 6 wherein said crosslinking molecule comprises a haloalkyl furocoumarin.

10. The probe of claim 6 wherein said crosslinking molecule comprises a haloalkyl benzodipyrone.

11. The probe of claim 6 wherein said crosslinking molecule comprises a haloalkyl courmarin.

12. The probe of claim 6 wherein said crosslinking molecule comprises an azido nucleoside triphosphate.

13. The probe of claim 6 wherein said crosslinking molecule comprises a member selected from the group consisting of:

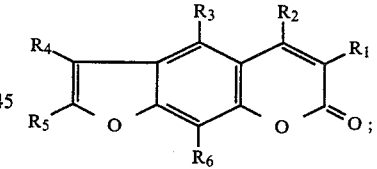

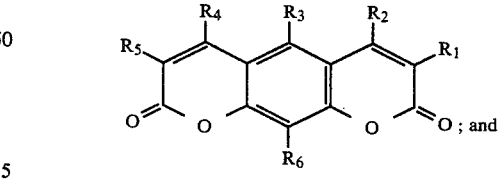

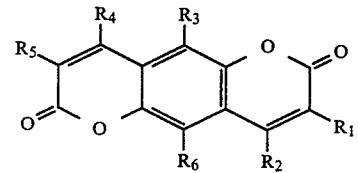

wherein R1 through R6 are the same or different and are each a member selected from the group consisting of H, CH$_3$, CH$_2$Cl, CH$_2$Br, CH$_2$I, CH$_2$OH, CH$_2$OCH$_3$, CH$_2$NH$_2$, N$_3$, COOH, COOCH$_3$, COOCH$_2$CH$_3$, NH$_2$, NO$_2$, CF$_3$, CCl$_3$, CH(CH$_3$)$_2$, C(CH$_3$)$_3$, Cl, Br, I and F.

14. A probe as recited in claim 8 wherein the crosslinking molecule comprises a member selected from the group consisting of psoralen, 8-methoxypsoralen, 5-methoxypsoralen, 4,5',8-trimethylpsoralen, 4'-hydroxymethyl -4,5',8-trimethylpsoralen and 4'-aminomethyl-4,5',8-trimethylpsoralen.

15. A probe as recited in claim 3 wherein said label is $^3H$ or $^{14}C$.

16. A method for determining the presence of specific nucleic acid base sequences in nucleic acid target molecules comprising:
  A. providing single stranded nucleic acid molecules having an essentially complementary base sequence to a defined region in the target molecules;
  B. attaching labeled crosslinking molecules to said single-stranded nucleic acid molecules which are capable of forming covalent crosslinks between said single stranded nucleic acid molecules and said target molecules;
  C. hybridizing said single stranded nucleic acid molecules to said defined region in said target molecules;
  D. forming covalent bonds between said labelled crosslinking molecules and target molecules; and
  E. measuring the amount of said labelled crosslinking molecules and single stranded nucleic acid molecules present on said target molecules.

17. The method of claim 16 further comprising, prior to the measuring step of sub-part E, separating the crosslinking molecules which have not formed covalent bonds with the target from those which have by techniques that differentiate between single stranded and double stranded complexes.

18. The method of claim 17, wherein said techniques are selected from the group consisting of gel filtration, hydroxylapatite chromatography, enzyme digestion, and photoreversal or chemical reversal of uncrosslinked molecules.

19. The method as recited in claim 16 wherein the crosslinking molecule is chosen from the group consisting of psoralen, 8-methoxypsoralen, 5-methoxypsoralen, 4,5',8-trimethylpsoralen, 4'-hydroxymethyl-4,5',8-trimethylpsoralen and 4'-aminomethyl-4,5',8-trimethylpsoralen.

20. The method as recited in claim 16 wherein the crosslinking molecule is labeled with a label chosen from the group consisting of radioactive nuclides, chromogenic labels, fluorogenic labels, chemiluminescent dyes and ligands.

21. The method as recited in claim 20 wherein said label is 3H or 14C.

22. The method as recited in claim 16 wherein the crosslinking molecule is a member chosen from the group consisting of furocoumarins, benzodipyrones and bis azides.

23. The method as recited in claim 16 wherein said covalent bonds are formed chemically.

24. The method as recited in claim 16 wherein said covalent bonds are formed photochemically.

25. The method of claim 17 wherein said single stranded nucleic acid molecule comprises an RNA probe and said target comprises a DNA molecule and wherein said technique comprises alkaline hydrolysis.

26. A method for determining the presence of specific nucleic acid sequences in nucleic acid target molecules comprising:
  A. providing labeled single-stranded nucleic acid molecules having an essentially complementary base sequence to a defined region in the target molecules;
  B. attaching crosslinking molecules to said labelled single-stranded nucleic acid molecules which are capable of forming covalent crosslinks between said labelled single-stranded nucleic acid molecules and said target molecules;
  C. hybridizing said labelled single-stranded nucleic acid molecules to said defined region in said target molecules;
  D. forming covalent bonds between said crosslinking molecules and target molecules; and
  E. measuring the amount of said labelled single-stranded nucleic acid molecules covalently bonded to said target molecules.

27. A method for determining the presence of specific nucleic acid base sequences in labelled nucleic acid target molecules comprising:
  A. providing single-stranded nucleic acid molecules having an essentially complementary base sequence to a defined region in the labelled target molecules;
  B. attaching crosslinking molecules to said single-stranded nucleic acid molecules which are capable of forming covalent crosslinks between said single-stranded nucleic acid molecules and said labelled target molecules;
  C. hybridizing said single-stranded nucleic acid molecules to said defined region in said labelled target molecules;
  D. forming covalent bonds between said crosslinking molecules and target molecules; and
  E. measuring the amount of said labelled target molecules covalently crosslinked to said single-stranded nucleic acid molecules.

28. The method of claims 16, 26 or 27 wherein said single-stranded nucleic acid molecules are chemically linked to a solid support.

29. The method of claim 28 wherein said solid support comprises silicon.

30. The method of claim 29 wherein said solid support comprises controlled pore glass.

31. The probe of claim 1 wherein said crosslinking molecule comprises a member selected from the group consisting of furocoumarins and benzodipyrones monoadducted to pyrimidine via cyclobutane bridge linkage.

32. The method of any one of claims 16, 26 or 27 wherein said single-stranded nucleic acid molecules are attached to a crosslinking molecule comprising a member selected from the group consisting of furocoumarins and benzodipyrones by direct incorporation during chemical synthesis of said single-stranded nucleic acid molecule.

33. A probe for determining the presence of specific nucleic acid based sequences in nucleic acid target molecules comprising:
  labeled single-stranded nucleic acid molecules having essentially complementary based sequences to defined regions in the nucleic acid target molecules; and
  crosslinking molecules attached to said single-stranded nucleic acid molecules which are capable of forming covalent crosslinking between said single-stranded nucleic acid molecules and said target molecules, whereby the presence of said specific nucleic acid base sequences determined by measuring the amount of labeled probe covalently bound.

34. The probe of claim 33 wherein said label is radioactive.

35. A probe as recited in claim 33 wherein the single-stranded nucleic acid molecule is labeled with a member selected from the group consisting of radioactive nuclides, chromogenic labels, fluorogenic labels, chemiluminescent dyes and ligands.

36. A reagent for DNA synthesis comprising a pyrimidine monophosphoramadite nucleoside furan-side monoadducted to a member selected from the group consisting of

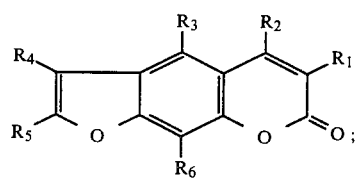

-continued wherein $R_1$–$R_6$ are the same or different and are each a member selected from the group consisting of H, $CH_3$, $CH_2Cl$, $CH_2Br$, $CH_2I$, $CH_2OH$, $CH_2OCH_3$, $CH_2NH_2$, $N_3$, COOH, $COOCH_3$, $COOCH_2CH_3$, $NH_2$, $NO_2$, $CF_3$, $CCl_3$, $CH(CH_3)_2$, $C(CH_3)_3$, Cl, Br, I and F.

37. A reagent as recited in claim 36 wherein the molecule comprises a member selected from the group consisting of psoralen, 8-methoxypsoralen, 5-methoxypsoralen, 4,5′,8-trimethylpsoralen, 4′-hydroxymethyl, 4,5′,8-trimethylpsoralen, and 4′-aminomethyl-4,5′8-trimethylpsoralen.

* * * * *

UNITED STATES PATENT AND TRADEMARK OFFICE
CERTIFICATE OF CORRECTION

PATENT NO. : 4,599,303
DATED : July 8, 1986
INVENTOR(S) : Kenichi K. Yabusaki et al.

It is certified that error appears in the above—identified patent and that said Letters Patent is hereby corrected as shown below:

In Column 20, line 19, "$Ch_2Cl$" should be --$CH_2Cl$--.

Signed and Sealed this
Seventh Day of October, 1986

[SEAL]

*Attest:*

DONALD J. QUIGG

*Attesting Officer*          *Commissioner of Patents and Trademarks*

UNITED STATES PATENT AND TRADEMARK OFFICE
CERTIFICATE OF CORRECTION

PATENT NO. : 4,599,303

DATED : July 8, 1986

INVENTOR(S) : KENICHI K. YABUSAKI et al.

It is certified that error appears in the above—identified patent and that said Letters Patent is hereby corrected as shown below:

In Column 17, line 31, between the words "target" and "from", add --molecules--.

In Column 18, line 64, "crosslinking" should be --crosslinks--.

Signed and Sealed this

Fourteenth Day of June, 1988

Attest:

DONALD J. QUIGG

Attesting Officer     Commissioner of Patents and Trademarks